(12) United States Patent
Yoshikawa et al.

(10) Patent No.: US 8,168,816 B2
(45) Date of Patent: May 1, 2012

(54) METHOD FOR PRODUCING PURIFIED FORMYLCYCLOPROPANE COMPOUND AND INTERMEDIATE OF SUCH FORMYLCYCLOPROPANE COMPOUND

(75) Inventors: Kouji Yoshikawa, Osaka (JP); Ryo Minamida, Kyoto (JP); Makoto Itagaki, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 878 days.

(21) Appl. No.: 12/095,608

(22) PCT Filed: Dec. 12, 2006

(86) PCT No.: PCT/JP2006/325141
§ 371 (c)(1),
(2), (4) Date: Jul. 14, 2008

(87) PCT Pub. No.: WO2007/069759
PCT Pub. Date: Jun. 21, 2007

(65) Prior Publication Data
US 2010/0305353 A1 Dec. 2, 2010

(30) Foreign Application Priority Data
Dec. 13, 2005 (JP) ................. 2005-358631

(51) Int. Cl.
*C07C 67/313* (2006.01)
*C07C 69/757* (2006.01)
*C07C 303/32* (2006.01)
*C07C 309/19* (2006.01)

(52) U.S. Cl. ...................................... 560/124

(58) Field of Classification Search ......................... None
See application file for complete search history.

(56) References Cited

U.S. PATENT DOCUMENTS

| 3,723,469 | A | 3/1973 | Martel |
| 5,471,004 | A | 11/1995 | Kaneko et al. |
| 2005/0090685 | A1 | 4/2005 | Yoshikawa |
| 2005/0240050 | A1* | 10/2005 | Minamida et al. ............ 560/124 |

FOREIGN PATENT DOCUMENTS

| JP | 2-275834 A | 11/1990 |
| JP | 7-61948 A | 3/1995 |
| JP | 2002-249457 A | 9/2002 |
| JP | 2004-99595 A | 4/2004 |

OTHER PUBLICATIONS

D.P. Kjell et al., Journal of Organic Chemistry, (1999), vol. 64, No. 15, pp. 5722-572 Experimental Section.

* cited by examiner

*Primary Examiner* — Daniel Sullivan
*Assistant Examiner* — Yevegeny Valenrod
(74) *Attorney, Agent, or Firm* — Sughrue Mion, PLLC

(57) ABSTRACT

A method for producing a purified formylcyclopropane compound represented by the formula (1) comprising (A) a step of reacting a crude formylcyclopropane compound represented by the formula (1):

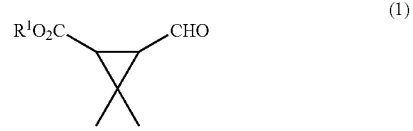

wherein $R^1$ represents an alkyl group or the like, with an alkali metal hydrogen sulfite to obtain an alkali metal hydroxymethanesulfonate represented by the formula (2):

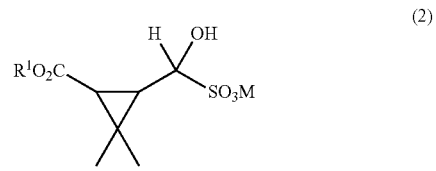

wherein $R^1$ represents the same meaning as defined above and M represents an alkali metal, and
(B) a step of reacting an acid, a base or a water-soluble aldehyde with the alkali metal hydroxymethanesulfonate represented by the formula (2) obtained in the above-mentioned step (A) to obtain a purified formylcyclopropane compound represented by the formula (1).

4 Claims, No Drawings

METHOD FOR PRODUCING PURIFIED FORMYLCYCLOPROPANE COMPOUND AND INTERMEDIATE OF SUCH FORMYLCYCLOPROPANE COMPOUND

TECHNICAL FIELD

The present invention relates to a method for producing a purified formylcyclopropane compound and an intermediate of such formylcyclopropane compound.

BACKGROUND ART

A formylcyclopropane compound represented by the formula (1) is an important compound as a synthetic intermediate of pyrethroid household agents for epidemic prevention, insecticides and the like. As methods for producing such formylcyclopropane compound, a method comprising oxidizing 2,2-dimethyl-3-hydroxymethylcyclopropanecarboxylic acid ester (e.g. JP 2004-99595 A), a method comprising oxidizing 2,2-dimethyl-3-(2-methyl-1-propenyl) cyclopropanecarboxylic acid ester with an oxidizing agent such as sodium periodate, ozone and the like (e.g. JP 2003-267915 A and JP 46-24695 B) and the like have been known.

A crude formylcyclopropane compound obtained by these methods contains by-products generating in the reaction and impurities derived from raw materials, and usually, a purified formylcyclopropane compound is obtained by distillation of the crude formylcyclopropane compound under reduced pressure as described in JP 46-24695 B. However, since a cyclopropane skeleton is thermally unstable, it was necessary to conduct a reduced pressure distillation of the crude formylcyclopropane compound under a high vacuum condition and burden of facility was great. Furthermore, it was difficult to remove impurities having a near vapor pressure to the formylcyclopropane compound. Therefore, a development of a more industrial method for producing a purified formylcyclopropane compound has been expected.

DISCLOSURE OF THE INVENTION

The present invention provides a method for producing a purified formylcyclopropane compound represented by the formula (1) comprising (A) a step of reacting a crude formylcyclopropane compound represented by the formula (1):

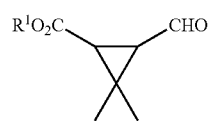

(1)

wherein $R^1$ represents an alkyl group which may be substituted with at least one selected from a group consisting of a halogen atom, a C1-C3 alkoxy group and a C6-C10 aryloxy group; an aryl group which may be substituted with at least one selected from a group consisting of a halogen atom, a C1-C3 alkoxy group and a C6-C10 aryloxy group; a heteroaryl group which may be substituted with at least one selected from a group consisting of a halogen atom, a C1-C3 alkoxy group and a C6-C10 aryloxy group; or an aralkyl group which may be substituted with at least one selected from a group consisting of a halogen atom, a C1-C3 alkoxy group and a C6-C10 aryloxy group, with an alkali metal hydrogen sulfite to obtain an alkali metal hydroxymethanesulfonate represented by the formula (2):

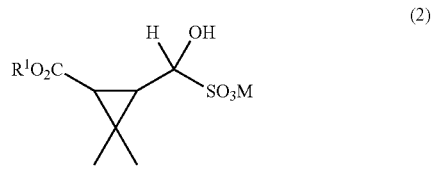

(2)

wherein $R^1$ represents the same meaning as defined above and M represents an alkali metal, and
(B) a step of reacting an acid, a base or a water-soluble aldehyde with the alkali metal hydroxymethanesulfonate represented by the formula (2) obtained in the above-mentioned step (A) to obtain a purified formylcyclopropane compound represented by the formula (1), and the above-mentioned alkali metal hydroxymethanesulfonate represented by the formula (2).

BEST MODE FOR CARRYING OUT THE PRESENT INVENTION

First, the step (A) will be illustrated.
In the formula of the formylcyclopropane compound represented by the formula (1) (hereinafter, simply referred to as the formylcyclopropane compound (1)), $R^1$ represents an alkyl group which may be substituted with at least one selected from a group consisting of a halogen atom, a C1-C3 alkoxy group and a C6-C10 aryloxy group; an aryl group which may be substituted with at least one selected from a group consisting of a halogen atom, a C1-C3 alkoxy group and a C6-C10 aryloxy group; a heteroaryl group which may be substituted with at least one selected from a group consisting of a halogen atom, a C1-C3 alkoxy group and a C6-C10 aryloxy group; or an aralkyl group which may be substituted with at least one selected from a group consisting of a halogen atom, a C1-C3 alkoxy group and a C6-C10 aryloxy group.

Examples of the alkyl group include a linear, branched chain or cyclic C1-C10 alkyl group such as a methyl group, an ethyl group, an n-propyl group, an isopropyl group, a cyclopropyl group, an n-butyl group, an isobutyl group, a sec-butyl group, a tert-butyl group, an n-pentyl group, a cyclopentyl group, an n-hexyl group, a cyclohexyl group and a menthyl group. The alkyl group may be substituted with at least one selected from a group consisting of a halogen atom, a C1-C3 alkoxy group and a C6-C10 aryloxy group.

Examples of the halogen atom include a fluorine atom, a chlorine atom and a bromine atom. Examples of the C1-C3 alkoxy group include a methoxy group, an ethoxy group, an n-propoxy group and an isopropoxy group. Examples of C6-C10 aryloxy group include a phenoxy group and a naphthoxy group.

Examples of the alkyl group substituted with at least one selected from a group consisting of a halogen atom, a C1-C3 alkoxy group and a C6-C10 aryloxy group include a trifluoromethyl group, a pentafluoroethyl group, a 2-ethoxyethyl group and a 2-phenoxyethyl group.

Examples of the aryl group include a C6-C10 aryl group such as a phenyl group, a 4-methylphenyl group and a naphthyl group. Examples of the aryl group substituted with at least one selected from a group consisting of a halogen atom, a C1-C3 alkoxy group and a C6-C10 aryloxy group include a 4-fluorophenyl group, a 3-phenoxyphenyl group, a 2,3,5,6-tetrafluorophenyl group, a 2,3,5,6-tetrafluoro-4-methylphenyl group, a 2,3,5,6-tetrafluoro-4-methoxyphenyl group and a 2,3,5,6-tetrafluoro-4-methoxymethylphenyl group.

Examples of the heteroaryl group include a C4-C12 heteroaryl group such as a furyl group and an oxazolyl group. Examples of the heteroaryl group substituted with at least one selected from a group consisting of a halogen atom, a C1-C3 alkoxy group and a C6-C10 aryloxy group include a 3-methoxy-2-furyl group and a 3-fluoro-2-furyl group.

Examples of the aralkyl group include a C7-C20 aralkyl group such as a benzyl group and a phenethyl group. Examples of the aralkyl group substituted with at least one selected from a group consisting of a halogen atom, a C1-C3 alkoxy group and a C6-C10 aryloxy group include a 4-fluorobenzyl group, a 3-phenoxybenzyl group, a 2,3,5,6-tetrafluorobenzyl group, a 2,3,5,6-tetrafluoro-4-methylbenzyl group, a 2,3,5,6-tetrafluoro-4-methoxybenzyl group and a 2,3,5,6-tetrafluoro-4-methoxymethylbenzyl group.

Examples of the formylcyclopropane compound (1) include methyl 2,2-dimethyl-3-formylcyclopropanecarboxylate, ethyl 2,2-dimethyl-3-formylcyclopropanecarboxylate, n-propyl 2,2-dimethyl-3-formylcyclopropanecarboxylate, isopropyl 2,2-dimethyl-3-formylcyclopropanecarboxylate, n-butyl 2,2-dimethyl-3-formylcyclopropanecarboxylate, isobutyl 2,2-dimethyl-3-formylcyclopropanecarboxylate, tert-butyl 2,2-dimethyl-3-formylcyclopropanecarboxylate, benzyl 2,2-dimethyl-3-formylcyclopropanecarboxylate, 3-phenoxybenzyl 2,2-dimethyl-3-formylcyclopropanecarboxylate, 2,3,5,6-tetrafluorobenzyl 2,2-dimethyl-3-formylcyclopropanecarboxylate, 2,3,5,6-tetrafluoro-4-methylbenzyl 2,2-dimethyl-3-formylcyclopropanecarboxylate, 2,3,5,6-tetrafluoro-4-methoxybenzyl 2,2-dimethyl-3-formylcyclopropanecarboxylate and 2,3,5,6-tetrafluoro-4-methoxymethylbenzyl 2,2-dimethyl-3-formylcyclopropanecarboxylate.

The formylcyclopropane compound (1) has two asymmetric carbon atoms on the cyclopropane ring and four kinds of isomers exist. Any one of isomers may be used and a mixture of two or more isomers may be used.

The crude formylcyclopropane compound (1) can be produced by a known method, for example, a method comprising oxidizing a 3-hydroxymethylcyclopropane compound represented by the formula (3):

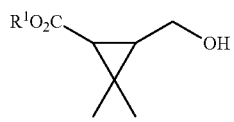

(3)

wherein R$^1$ represents the same meaning as defined above (e.g. JP 2004-99595 A), a method comprising reacting 3-(2-methyl-1-propenyl)cyclopropane compound represented by the formula (4):

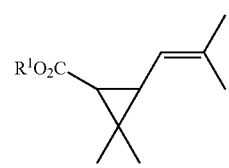

(4)

wherein R$^1$ represents the same meaning as defined above, with an oxidizing agent such as sodium periodate, ozone and the like (e.g. JP 2003-267915 A and JP 46-24695 B) and the like.

The crude formylcyclopropane compound (1) is one containing impurities which contains in raw materials and byproducts generating in the reaction such as 6,6-dimethyl-3-oxa-2-oxobicyclo[3.1.0]hexane, 3-carboxycyclopropane compound and 3-alkoxycarbonylcyclopropane compound.

Meanwhile, in the present description, the trans-isomer means one having the ester group at 1-position and the substituent at 3-position on the opposite side with respect to the cyclopropane ring plane and the cis-isomer means one having the ester group at 1-position and the substituent at 3-position on the same side with respect to the cyclopropane ring plane.

While kinds and contents of impurities and by-products contained in the crude formylcyclopropane compound (1) differ depending on raw materials used, a reaction condition and the like, the total of impurities and reaction by-products is usually 0.1% by weight or more per 1 part of the formylcyclopropane compound (1) in the crude formylcyclopropane compound (1).

The step (A) is a step of reacting the crude formylcyclopropane compound (1) with an alkali metal hydrogen sulfite to obtain an alkali metal hydroxymethanesulfonate represented by the formula (2):

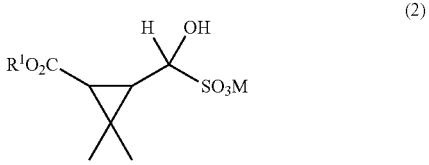

(2)

wherein R$^1$ represents the same meaning as defined above and M represents an alkali metal.

Examples of the alkali metal hydrogen sulfite include sodium hydrogen sulfite and potassium hydrogen sulfite. While a solid alkali metal hydrogen sulfite may be used and an aqueous alkali metal hydrogen sulfite solution may be used, the aqueous alkali metal hydrogen sulfite solution is preferably used. While the concentration of the alkali metal hydrogen sulfite in the aqueous alkali metal hydrogen sulfite solution is not particularly limited, it is usually 5 to 35% by weight.

The used amount of the alkali metal hydrogen sulfite is usually 0.8 mole or more per 1 mole of the formylcyclopropane compound (1). While there is no particular upper limit, the practical used amount is 1 to 2 moles per 1 mole of the formylcyclopropane compound (1) from an economic point.

While the reaction of the formylcyclopropane compound (1) and the alkali metal hydrogen sulfite may be conducted in the absence of a solvent, it is preferably conducted in the presence of a water-nonmiscible organic solvent or a mixed solvent of a water-nonmiscible organic solvent and water. Examples of the water-nonmiscible organic solvent include aromatic hydrocarbon solvents such as toluene, xylene and mesitylene; aliphatic hydrocarbon solvents such as pentane, hexane, heptane, octane and cyclohexane; ester solvents such as ethyl acetate and methyl benzoate; halogenated hydrocarbon solvents such as dichloromethane, dichloroethane, carbon tetrachloride and chlorobenzene; nitrile solvents such as benzonitrile; and ether solvents such as diethyl ether. The water-nonmiscible organic solvent may be used alone and two or more kinds thereof may be mixed to use. While the used amount of the water-nonmiscible organic solvent is not particularly limited, it is usually 0.5 to 10 parts by weight and preferably 1 to 5 parts by weight per 1 part of the formylcyclopropane compound (1). While the used amount of water is not particularly limited, it is usually 0.5 to 10 parts by weight and preferably 1 to 5 parts by weight per 1 part of the formylcyclopropane compound (1). When the aqueous alkali metal hydrogen sulfite solution is used, the used amount of water may be decided in consideration to the amount of water in the aqueous solution.

The reaction temperature is usually 0 to 80° C. and preferably 10 to 50° C.

The reaction of the formylcyclopropane compound (1) and the alkali metal hydrogen sulfite is conducted by mixing the formylcyclopropane compound (1) with the alkali metal hydrogen sulfite, as necessary in the presence of a solvent. The mixing order is not particularly limited.

The reaction is usually conducted at normal pressure and may be conducted under pressure. The progress of the reaction can be checked by a conventional analytical means such as gas chromatography, high performance liquid chromatography, thin layer chromatography and the like.

The alkali metal hydroxymethanesulfonate represented by the formula (2) (hereinafter, simply referred to as the alkali metal hydroxymethanesulfonate (2)) is obtained by a reaction of the formylcyclopropane compound (1) and the alkali metal hydrogen sulfite.

Examples of the alkali metal hydroxymethanesulfonate (2) include sodium hydroxy[3-(methoxycarbonyl)-2,2-dimethylcyclopropyl]methanesulfonate, sodium hydroxy[3-(ethoxycarbonyl)-2,2-dimethylcyclopropyl]methanesulfonate, sodium hydroxy[3-(n-propoxycarbonyl)-2,2-dimethylcyclopropyl]methanesulfonate, sodium hydroxy[3-(isopropoxycarbonyl)-2,2-dimethylcyclopropyl]methanesulfonate, sodium hydroxy[3-(n-butoxycarbonyl)-2,2-dimethylcyclopropyl]methanesulfonate, sodium hydroxy[3-(isobutoxycarbonyl)-2,2-dimethylcyclopropyl]methanesulfonate, sodium hydroxy[3-(tert-butoxycarbonyl)-2,2-dimethylcyclopropyl]methanesulfonate, sodium hydroxy[3-(benzyloxycarbonyl)-2,2-dimethylcyclopropyl]methanesulfonate, sodium hydroxy[3-(3-phenoxybenzyloxycarbonyl)-2,2-dimethylcyclopropyl]methanesulfonate, sodium hydroxy[3-(2,3,5,6-tetrafluorobenzyloxycarbonyl)-2,2-dimethylcyclopropyl]methanesulfonate, sodium hydroxy[3-(2,3,5,6-tetrafluoro-4-methylbenzyloxycarbonyl)-2,2-dimethylcyclopropyl]methanesulfonate, sodium hydroxy[3-(2,3,5,6-tetrafluoro-4-methoxybenzyloxycarbonyl)-2,2-dimethylcyclopropyl]methanesulfonate, sodium hydroxy[3-(2,3,5,6-tetrafluoro-4-methoxymethylbenzyloxycarbonyl)-2,2-dimethylcyclopropyl]methanesulfonate, and the above-mentioned each compound of which sodium is changed to potassium (for example, potassium hydroxy[3-(methoxycarbonyl)-2,2-dimethylcyclopropyl]methanesulfonate etc.) and the like.

After completion of the reaction, for example, an aqueous layer containing the alkali metal hydroxymethanesulfonate (2) can be obtained by conducting a separation treatment, as necessary after adding water or a water-nonmiscible organic solvent. The obtained aqueous layer containing the alkali metal hydroxymethanesulfonate (2) is used in the next step (B) as it is or as necessary, after washing with a water-nonmiscible organic solvent.

Alternatively, the alkali metal hydroxymethanesulfonate (2) can be isolated by concentrating the obtained aqueous layer containing the alkali metal hydroxymethanesulfonate (2), and the isolated alkali metal hydroxymethanesulfonate (2) is used in the next step (B) as it is or after purifying by a conventional purification means such as recrystallization and the like.

Depending on a kind of the alkali metal hydroxymethanesulfonate (2) and the reaction condition, the alkali metal hydroxymethanesulfonate (2) sometimes is precipitated in the reaction mixture. In this case, the alkali metal hydroxymethanesulfonate (2) may be isolated by a filtration of the reaction mixture.

Next, the step (B) will be illustrated.

The step (B) is a step of reacting the alkali metal hydroxymethanesulfonate (2) obtained in the above step (A) with an acid, a base or a water-soluble aldehyde to obtain a purified formylcyclopropane compound represented by the formula (1).

Examples of the acid include inorganic acids such as hydrochloric acid, sulfuric acid and nitric acid; and sulfonic acids such as methanesulfonic acid.

Examples of the base include alkali metal hydroxides such as sodium hydroxide and potassium hydroxide; alkali metal carbonates such as sodium carbonate and potassium carbonate; and alkali metal hydrogen carbonates such as sodium hydrogen carbonate and potassium hydrogen carbonate, and the alkali metal hydroxides and alkali metal carbonates are preferable.

Examples of the water-soluble aldehyde include monomers of the water-soluble aldehyde such as formaldehyde and acetaldehyde; and polymers of the water-soluble aldehyde such as trioxane, paraformaldehyde and paraldehyde.

Each of these acids, bases and water-soluble aldehydes may be used as it is and in a form of aqueous solution. The aqueous solution thereof is preferably used.

Among them, bases and water-soluble aldehydes are preferable.

The reaction of the alkali metal hydroxymethanesulfonate (2) with an acid, a base or a water-soluble aldehyde is usually conducted in the presence of a mixed solvent of a water-nonmiscible organic solvent and water.

While the used amount of water is not particularly limited, it is usually 0.5 to 20 parts by weight and preferably 1 to 5 parts by weight per 1 part of the alkali metal hydroxymethanesulfonate (2). When an aqueous layer containing the alkali metal hydroxymethanesulfonate (2) obtained in the above-mentioned step (A) or an aqueous solution of the acid, the base or the water-soluble aldehyde is used, the used amount of water may be decided in consideration to the amount of water in these aqueous layer or the aqueous solution.

Examples of the water-nonmiscible organic solvent include the same as exemplified in the above-mentioned step (A). While the used amount of the water-nonmiscible organic solvent is not particularly limited, it is usually 0.5 to 10 parts by weight and preferably 1 to 5 parts by weight per 1 part of the alkali metal hydroxymethanesulfonate (2).

When the acid is used, the used amount of the acid is usually 0.8 to 1.5 molar equivalent per 1 mole of the alkali metal hydroxymethanesulfonate (2).

When the base is used, the used amount of the base is usually 0.8 molar equivalent or more per 1 mole of the alkali metal hydroxymethanesulfonate (2). When the used amount of the base is too much, the formylcyclopropane compound (1) is decomposed easily, and therefore, practically, the base is preferable used in an amount by which the pH of an aqueous layer of the reaction mixture is adjusted to a range of 9 to 11, and more preferably to a range of 9.5 to 10.5.

Meanwhile, in the present description, the molar equivalent means a value obtained by multiplying a number of moles of the acid or base by the valence. For example, when 0.5 mole of sulfuric acid is used per 1 mole of the hydroxymethanesulfonate (2), the used amount of sulfuric acid is 1 molar equivalent, and when 0.5 mole of potassium carbonate is used per 1 mole of the hydroxymethanesulfonate (2), the used amount of potassium carbonate is 1 molar equivalent When the water-soluble aldehyde is used, the used amount of the water-soluble aldehyde is usually 0.8 mole or more per 1 mole of the alkali metal hydroxymethanesulfonate (2). While the used amount thereof is not particularly limited, it is practically 1 to 3 moles per 1 mole of the alkali metal hydroxymethanesulfonate (2) from an economic point. When the polymer such as paraformaldehyde is used, the polymer is converted to the corresponding monomer based on the polymerization degree and the polymer in an amount of 0.8 mole or more as the monomer per 1 mole of the alkali metal hydroxymethanesulfonate (2) is usually used. For example, when trioxane is used, 1 mole of trioxane is converted to 3 moles of formaldehyde, and the used amount may be decided. Alternatively, when the polymerization degree of the polymer is not clear, the used amount thereof may be decided assuming that a value obtained by dividing organic layer.

In the present invention, "the purified formylcyclopropane compound (1)" means one in which the amount of impurities and by-products containing in the crude formylcyclopropane compound (1) used in the above-mentioned step (A) is decreased and of which chemical purity is improved. The chemical purity can be calculated by a conventional analytical means such as gas chromatography, high performance liquid chromatography, thin layer chromatography, NMR and the like.

Alternatively, the purified formylcyclopropane compound (1) obtained may be further purified by a conventional purification means such as distillation, recrystallization, column chromatography and the like.

Alternatively, when the formylcyclopropane compound (I) in the crude formylcyclopropane compound (1) used in the above-mentioned step (A) is an optically active isomer, the formylcyclopropane compound (1) in the purified formylcyclopropane compound (1) obtained is usually also an optically active isomer.

EXAMPLES

The present invention is illustrated by Examples in more detail below, but the present invention is not limited to these Examples. The chemical purity was calculated by the weight of the polymer by the molecular weight of the corresponding monomer is number of moles of the corresponding monomer.

The temperature of the reaction of the alkali metal hydroxymethanesulfonate (2) with an acid, a base or a water-soluble aldehyde is usually 0 to 80° C., and preferably 20 to 60° C.

The reaction is usually conducted by mixing the alkali metal hydroxymethanesulfonate (2) with an acid, a base or a water-soluble aldehyde in the presence of the water-nonmiscible organic solvent and water. While the mixing order is not particularly limited, the acid, the base or the water-soluble aldehyde is preferably added to a mixture of the water-nonmiscible organic solvent, water and the alkali metal hydroxymethanesulfonate (2).

The reaction is usually conducted at normal pressure and may be conducted under pressure. The progress of the reaction can be checked by a conventional analytical means such as gas chromatography, high performance liquid chromatography, thin layer chromatography and the like.

After completion of the reaction, for example, an organic layer containing the formylcyclopropane compound (I) can be obtained by separating the reaction mixture, and the purified formylcyclopropane compound (1) can be isolated by, for example, concentrating the obtained gas chromatography area-percentage method and the content of impurities and by-products and the yield were calculated by gas chromatography internal standard method.

Example 1

To 179.0 g of toluene solution containing the crude methyl trans-2,2-dimethyl-3-formylcyclopropanecarboxylate (the content of methyl trans-2,2-dimethyl-3-formylcyclopropanecarboxylate: 27.9% by weight, the content of 6,6-dimethyl-3-oxa-2-oxobicyclo[3.1.0]hexane: 3.5% by weight), 55.7 g of water was added and then 115.0 g of a 35% by weight aqueous solution of sodium hydrogen sulfite was added dropwise thereto at 25° C. The obtained mixture was stirred at 25° C. for 2 hours to effect reaction. After leaving the reaction mixture at rest, the reaction mixture was separated to an aqueous layer containing sodium hydroxy[3-(methoxycarbonyl)-2,2-dimethylcyclopropyl]methanesulfonate and an organic layer. To the obtained aqueous layer, 75.1 g of toluene was added and the resultant mixture was heated to 50° C. and then 66.8 g of 23% by weight aqueous solution of sodium hydroxide was added dropwise thereto. The reaction mixture obtained was stirred at 50° C. for 0.5 hour to effect reaction. The pH of the aqueous layer after completion of the addition was 9.9. After leaving the reaction mixture at rest, the reaction mixture was separated to an organic layer and an aqueous layer. To the obtained aqueous layer, 26 g of toluene and 0.9 g of 23% by weight aqueous solution of sodium hydroxide were added to adjust to pH 10.0 and the resultant mixture was stirred at 50° C. for 0.5 hour. After leaving the obtained mixture at rest, the mixture was separated to an organic layer and an aqueous layer. The organic layer obtained was mixed with the organic layer previously obtained to obtain 148.7 g of a toluene solution containing purified methyl trans-2,2-dimethyl-3-formylcyclopropanecarboxylate.

<Content>
Content of methyl trans-2,2-dimethyl-3-formylcyclopropanecarboxylate: 33.0% by weight, acquisition efficiency: 98%
Content of 6,6-dimethyl-3-oxa-2-oxobicyclo[3.1.0]hexane: 0.65% by weight, removal efficiency: 85%<
<Chemical Purity>
Chemical purity of crude trans-2,2-dimethyl-3-formylcyclopropanecarboxylate: 81.7%
Chemical purity of purified trans-2,2-dimethyl-3-formylcyclopropanecarboxylate: 93.6%

Example 2

To 121.6 g of toluene solution containing the crude methyl trans-2,2-dimethyl-3-formylcyclopropanecarboxylate (the content of methyl trans-2,2-dimethyl-3-formylcyclopropanecarboxylate: 24.7% by weight, the content of methyl trans-2,2-dimethyl-3-methoxycarbonylcyclopropanecarboxylate: 0.12% by weight), 69.2 g of a 35% by weight aqueous solution of sodium hydrogen sulfite was added dropwise at 25° C. The obtained mixture was stirred at 25° C. for 2 hours to effect reaction. After leaving the reaction mixture at rest, the reaction mixture was separated to an aqueous layer containing sodium hydroxy[3-(methoxycarbonyl)-2,2-dimethylcyclopropyl]methanesulfonate and an organic layer. To the obtained aqueous layer, 46.0 g of toluene was added and the resultant mixture was heated to 50° C. and then 28.6 g of 37% by weight aqueous formalin solution was added dropwise thereto. The reaction mixture obtained was stirred at 50° C. for 2 hours to effect reaction. After leaving the reaction mixture at rest, the reaction mixture was separated to an organic layer and an aqueous layer. To the obtained aqueous layer, 16.2 g of toluene was added and the resultant mixture was stirred at 50° C. for 1 hour. After leaving the obtained mixture at rest, the mixture was separated to an organic layer and an aqueous layer. The organic layer obtained was mixed with the organic layer previously obtained to obtain 75.1 g of a toluene solution containing purified methyl trans-2,2-dimethyl-3-formylcyclopropanecarboxylate.

<Content>
Content of methyl trans-2,2-dimethyl-3-formylcyclopropanecarboxylate: 31.3% by weight, acquisition efficiency: 96%
Content of methyl trans-2,2-dimethyl-3-formylcyclopropanecarboxylate: 0.04% by weight or less, removal efficiency: 80% or more <Chemical Purity>
Chemical purity of crude trans-2,2-dimethyl-3-formylcyclopropanecarboxylate: 98.5%
Chemical purity of purified trans-2,2-dimethyl-3-formylcyclopropanecarboxylate: 99.5%

Example 3

Ten point four gram of methyl trans-2,2-dimethyl-3-methoxycarbonylcyclopropanecarboxylate (content: 98.0% by weight) was dissolved in 12 g of toluene. TO the obtained solution, 9.9 g of a 35% by weight aqueous solution of sodium hydrogen sulfite was added dropwise at 25° C. The obtained mixture was stirred at 25° C. for 2 hours to effect reaction. After completion of the reaction, the reaction mixture was left at rest and then was separated to an organic layer and an aqueous layer. The obtained aqueous layer was concentrated under reduced pressure. The concentration residue obtained was dissolved in ethanol and then the resultant solution was concentrated under reduced pressure to obtain 8.6 g of a white solid of sodium hydroxy[3-(methoxycarbonyl)-2,2-dimethylcyclopropyl]methanesulfonate.

Melting point: 80 to 88° C.

$^1$H NMR (300 Hz, solvent: dimethyl sulfoxide-$d_6$) δ (ppm) 1.09 (s, 1.2H), 1.12 (s, 1.8H), 1.15 (s, 1.2H), 1.16 (s, 1.8H), 1.44-1.71 (m, 2H), 3.55 (s, 1.8H), 3.57 (s, 1.2H), 3.59-3.64 (m, 1H), 5.42-5.44 (m, 1H)

13C NMR (75.4 MHz, dimethyl sulfoxide-$d_6$)
δ (ppm) 20.4, 20.5, 21.3, 21.8, 25.4, 27.6, 29.8, 31.7, 33.9, 35.3, 51.1, 51.8, 81.2, 82.6, 171.7, 172.2

INDUSTRIAL APPLICABILITY

According to the present invention, the purified formylcyclopropane compound can be produced industrially advantageously from the crude formylcyclopropane compound.

The invention claimed is:

1. A method for producing a purified formylcyclopropane compound represented by the formula (1) comprising (A) a step of reacting a crude formylcyclopropane compound represented by the formula (1):

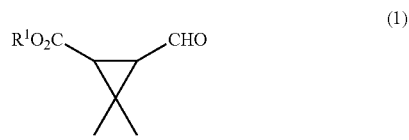

wherein $R^1$ represents an alkyl group which may be substituted with at least one selected from a group consisting of a halogen atom, a C1-C3 alkoxy group and a C6-C10 aryloxy group; an aryl group which may be substituted with at least one selected from a group consisting of a halogen atom, a C1-C3 alkoxy group and a C6-C 10 aryloxy group; a heteroaryl group which may be substituted with at least one selected from a group consisting of a halogen atom, a C1-C3 alkoxy group and a C6-C 10 aryloxy group; or an aralkyl group which may be substituted with at least one selected from a group consisting of a halogen atom, a C1-C3 alkoxy group and a C6-C10 aryloxy group, with an alkali metal hydrogen sulfite to obtain an alkali metal hydroxymethanesulfonate represented by the formula (2):

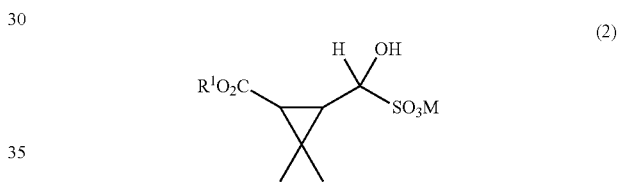

wherein $R^1$ represents the same meaning as defined above and M represents an alkali metal, and (B) a step of reacting a base with the alkali metal hydroxymethanesulfonate represented by the formula (2) obtained in the above-mentioned step (A) in a range of pH 9 to 11 to obtain a purified formylcyclopropane compound represented by the formula (1).

2. The method according to claim 1, wherein a reaction is conducted in an organic solvent using an aqueous solution of an alkali metal hydrogen sulfite in the step (A).

3. The method according to claim 2, wherein the reaction mixture is separated to an organic layer and an aqueous layer containing the alkali metal hydroxymethanesulfonate represented by the formula (2) in the step (A) and the aqueous layer is used in the step (B).

4. The method according to claim 1, wherein the base is an alkali metal hydroxide or an alkali metal carbonate.

* * * * *